United States Patent [19]
Raven

[11] Patent Number: 5,258,989
[45] Date of Patent: Nov. 2, 1993

[54] SOLID STATE LASER DIODE LIGHT SOURCE

[75] Inventor: Anthony Raven, Royston, England

[73] Assignee: Diomed Limited, Cambridge, England

[21] Appl. No.: 761,921

[22] PCT Filed: Feb. 12, 1991

[86] PCT No.: PCT/GB91/00207
  § 371 Date: Sep. 12, 1991
  § 102(e) Date: Sep. 12, 1991

[87] PCT Pub. No.: WO91/12641
  PCT Pub. Date: Aug. 22, 1991

[30] Foreign Application Priority Data
  Feb. 12, 1990 [GB] United Kingdom ............... 9003097

[51] Int. Cl.$^5$ ............................................. H01S 3/30
[52] U.S. Cl. ................................. 372/6; 372/101; 372/100; 372/106; 372/75; 359/669
[58] Field of Search ............... 372/92, 675, 102, 101, 372/100, 106; 359/669

[56] References Cited

U.S. PATENT DOCUMENTS

| | | | |
|---|---|---|---|
| 4,828,374 | 5/1989 | McCasun et al. | 359/669 |
| 4,890,289 | 12/1989 | Basu et al. | 372/75 |
| 4,904,068 | 2/1990 | Tatsuno et al. | 359/669 |
| 4,942,583 | 7/1990 | Nazarathy et al. | 372/102 |
| 5,005,180 | 4/1991 | Epelman et al. | 372/6 |
| 5,103,457 | 4/1992 | Wallace et al. | 372/92 |

OTHER PUBLICATIONS

Applied Optics, vol. 28, No. 21, 1 Nov. 1989, (New York, US) K. Tatsuno et al., "Deffraction-limited Circular single spot from phased aray lasers", pp. 4560-4568.

"High power, high efficient neodyium: yttrium aluminum garnet laser end pumped by a laser diode array", Applied Physics Letters, vol. 51, No. 16, 19 Oct. 1987, pp. 1212-1214.

"Scalable, end-pumped, diode-laser-pumped laser", T. Y. Fan, A. Sanchez and W. E. Defoe, Optics Letters, vol. 14, No. 19, 1 Oct. 1989.

"Pump Source Requirements for End-Pumped Lasers", T. Y. Fand and A. Sanchez, IEEE Journal of Quantum Electonics, vol. 26, No. 2, Feb. 1990.

Newport Research Corporation Catalogue No. 100 C 1987.

"Leger et al—Astigmatic ... Microlenses", SPIE, vol. 884.

Computer-Generated Holography II (1988), pp. 82-89.

Leger et al—"Coherent ... Coupling": Appl. Phys. Lett. Vol. 52(21) May 23, 1988, pp. 1771-1773.

*Primary Examiner*—Leon Scott, Jr.
*Attorney, Agent, or Firm*—Chilton, Alix & Van Kirk

[57] ABSTRACT

A laser diode light source comprises at least two laser diodes (1,2). The beams (3,4) of the diodes (1,2) are combined together by, for example, a polarising beam combiner (11) and the combined beam (18) is focused by a lens (19) onto an optical cable (20). The beams (3,4) are also acted on in the long direction of the laser stripes of the diodes (1,2) by anamorphic beam shaping means (7,8;9,10) to reduce the length of the image formed at the end of fibre (20) by a predetermined factor, chosen such that the numerical aperture of the focused beam (18) in said long direction does not substantially exceed that of the optical fibre (20).

15 Claims, 2 Drawing Sheets

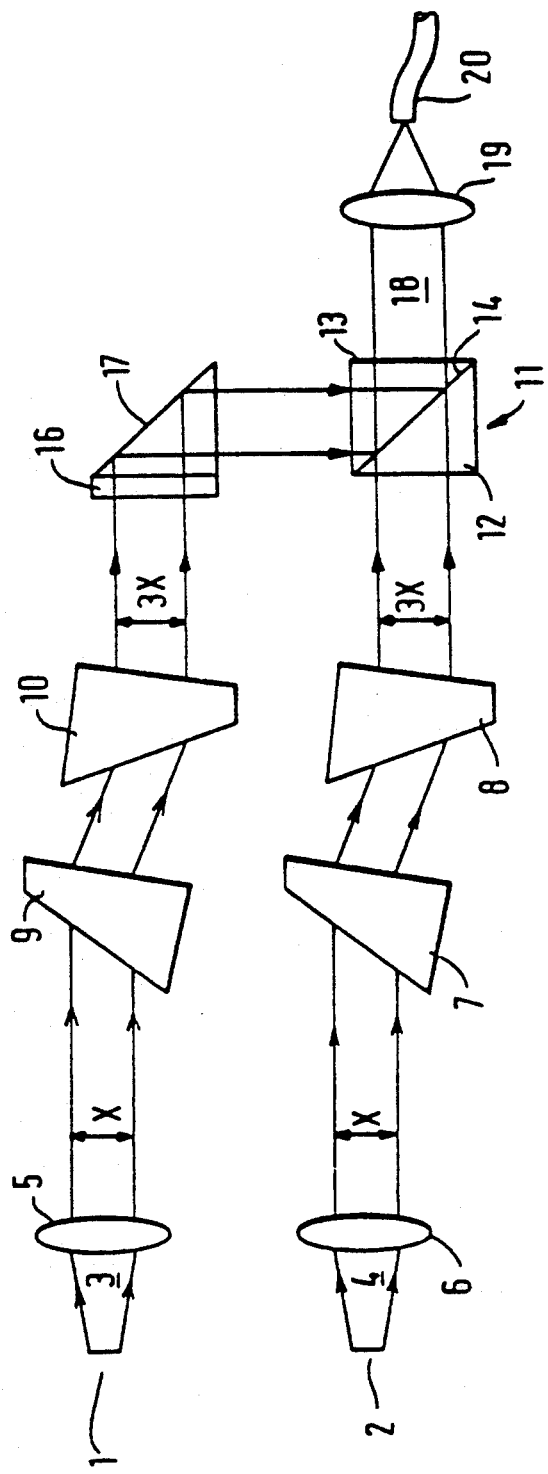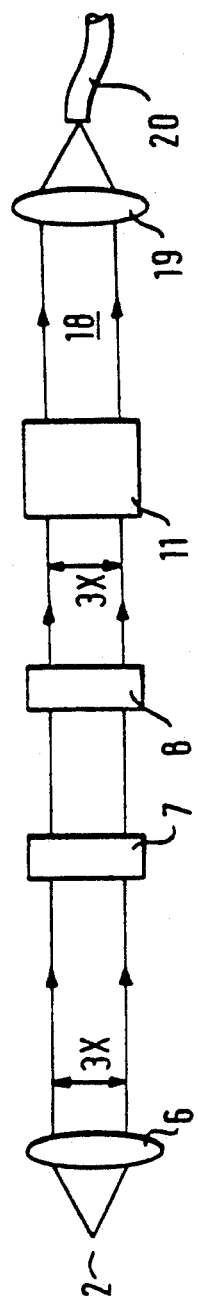

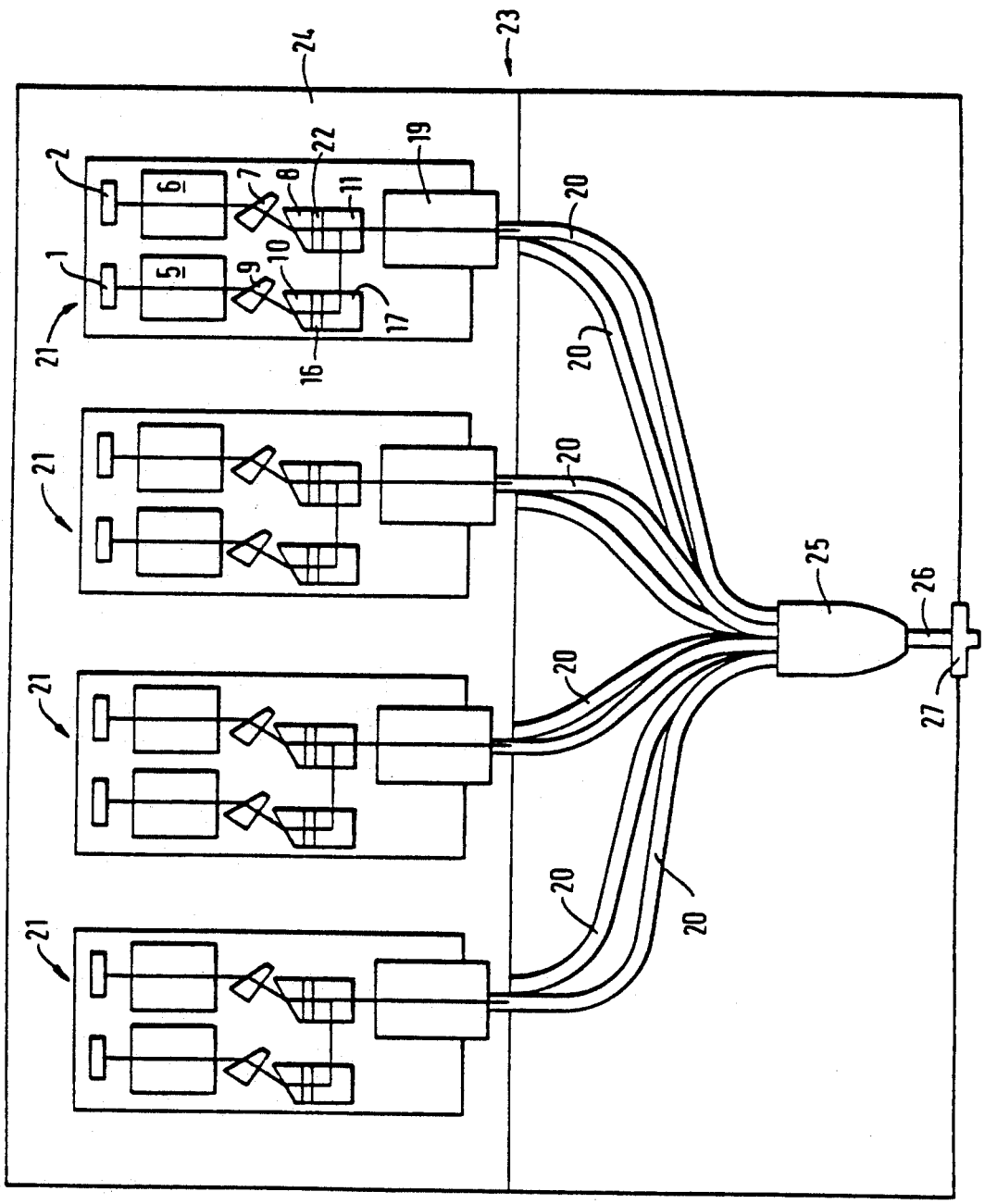

SOLID STATE LASER DIODE LIGHT SOURCE

The present invention relates to solid state laser diode light sources for use particularly, but not exclusively, in laser probes for treating tissue in applications such as laser angioplasty and contact laser surgery.

Medical laser devices for the treatment of e.g. blocked arteries are well known. Laser energy is directed through an optical fibre so as to either directly irradiate and destroy tissue, or indirectly irradiate and destroy tissue by heating a thermally conductive tip which contacts and destroys the tissue. In general, such devices have previously used gas lasers or solid state lasers such as Nd:YAG and as such are large and not easily portable. Semiconductor laser diodes have been used in ophthalmic surgery which requires relatively modest optical power ($\sim 1W$) since they provide an inexpensive, compact and robust source of laser light. However they have not been applied to other areas of surgery where higher powers are required because of the difficulty in coupling sufficient laser power from laser diodes into an optical fibre of sufficient flexibility and small diameter for use in surgical applications.

To provide a higher power laser diode light source from an optical fibre it has been proposed to use a plurality of laser diodes.

In one system, the light from each laser diode is fed into a respective optical fibre, a plurality of which are then bundled together to produce the required beam. However commercially available laser diodes produce a stripe source of light (typically $100 \times 1$ $\mu m$) rather than a point source which means that relatively large diameter optical fibres (which are traditionally circular) are required to contain the entire laser stripe, which if bundled together in sufficient numbers to give a suitable power output for surgical use, would result in an assembly which is too large for effective use in conjunction with a medical or surgical probe such as an angioplasty device. It has been proposed to deform the end portion of a circular fibre into a generally oblong shape with the intention that the output of the laser stripe may be more effectively captured and funnelled into a fibre of reduced diameter, but this is an expensive procedure and the funnelling is not energy efficient in practice.

According to a first aspect of the present invention there is provided a laser diode light source comprising at least two solid state laser diodes, a flexible optical fibre, and optical means, interposed between said diodes and said fibre, comprising means for combining the beams produced by said diodes into a combined beam and for focusing said combined beam into said fibre, wherein said optical means comprises an imaging means and anamorphic beam shaping means arranged such that the optical means produces at the fibre end a magnified combined image of the laser stripes of said diodes, the magnification being less in the long direction of the image stripe relative to the magnification in the width direction and being chosen such that the image stripe size in its long direction does not substantially exceed the core diameter of the fibre, the anamorphic beam shaping means being arranged to adjust the relative numerical apertures of the combined beam along said long and width directions such that the numerical apertures in said two directions of the beam focused into the end of the fibre do not substantially exceed the numerical aperture of the fibre.

In accordance with the invention, the optical power transmitted through the or each flexible fibre is increased with the result that a lesser number of fibres of smaller diameter may be conveniently bundled together to provide a source of sufficient brightness for e.g. surgical use within the size constraints imposed by an angioplasty or other medical device. A source in accordance with the invention may have other applications, such as laser soldering irons in which laser light passed through an optical fibre provides the heat for the soldering process. In such an application, the light from two laser diodes focused into a single optical fibre may provide sufficient power.

The invention enables the shape of the image to be optimised with respect to minimising the fibre core diameter without power losses arising due to numerical aperture mis-match. The magnified image stripe is a better fit with the end of a fibre core. Whilst the absolute value of magnifications in the long and width directions may vary (provided that relative magnification is less than one) depending on the application concerned and the size constraints imposed on the fibre, in many applications, it is desirable that the diameter of the or each fibre of such a source is minimized as far as possible without leading to power loss. In this case the optical means is effective to reduce the size of the image with respect to the source in the long direction of the stripes consistent with not substantially exceeding the numerical aperture of the fibre.

Commercially available laser diodes produce a beam of light from a stripe source, the beam having a lower numerical aperture along the direction of the stripe than perpendicular to the stripe. Typical values would be 0.1 NA and 0.33 NA respectively, which means that in the direction along the stripe, the numerical aperture of the beam is substantially less than that of a standard optical fibre, if, in the other direction, the beam and fibre numerical apertures approximately match one another.

With a circular fibre core, the minimum diameter is set by the length of the image of the laser source stripes formed at the fibre end, since if the diameter is less than the length of the image stripe, power will be lost as a result of the fibre not intersecting all of the beam. Moreover an optical means which reduces the length of the image stripe will result in a corresponding increase in divergence and thus in the numerical aperture of the combined beam focused onto the fibre end, and it is important that the beam numerical aperture does not significantly exceed that of the fibre if power loss is to be avoided.

As stated, in a preferred embodiment intended to minimise fibre diameter, the magnification provided by the optical means is chosen to reduce the length of the image stripe formed at the end of the fibre with respect to the source stripes by a certain factor chosen such that the numerical aperture of the combined focused beam does not substantially exceed that of the optical fibre and in the direction perpendicular to the stripes (in which direction the beam thickness does not impose size constraints on the fibre) the preferred optical means may have unit magnification provided that the beam numerical aperture in that direction also does not substantially exceed that of the fibre.

Thus, the core diameter of the fibre may be correspondingly reduced with resultant practical advantages in many applications, particularly where a plurality of fibres need to be bundled together into a closely packed array within certain size constraints.

In a particularly preferred embodiment the optical means is arranged such that the numerical aperture in the long direction of the image stripe of the beam focused onto the fibre end approximately matches the numerical aperture of the fibre. In this way, a maximum demagnification of the image in the long direction relative to the width direction and thus maximum optimising of image shape with respect to fibre core diameter may be achieved without power losses arising as a result of the beam's numerical aperture exceeding that of the fibre. The beam and fibre numerical apertures preferably match in the width direction also. In a preferred embodiment the optical means is arranged to decrease the length of the image stripe in the long direction relative to the width direction and increase the numerical aperture of the focused beam in the long direction by a factor of around 3. If the optical means has no effect on the beam in the direction perpendicular to the laser stripes, then with known diodes as described above it will be seen that the numerical apertures of the combined beam focused into the fibre will be substantially equal in the directions parallel and perpendicular to the stripe.

A preferred embodiment comprises means for collimating the beams from the laser diodes (which are normally divergent) located between the diodes and the beam combining means. This enables location of the beam combining means and, optionally, the beam shaping means between the diodes and the fibre without energy loss occurring as a result of beam divergence over the optical path between the diodes and fibre.

The preferred optical means comprises a collimating lens, an anamorphic telescope e.g. a pair of anamorphic prisms and an imaging lens. Such an arrangement acts, in the manner of a cylindrical telescope with magnification less than one in the long direction of the stripes relative to the width direction, whereby the length of the refocused, combined image of the stripes is reduced by the desired factor, for example around 3, relative to the width whilst the numerical aperture in such direction is correspondingly increased. The anamorphic telescope first acts relatively to widen the beam in this direction by a factor x, and the imaging lens produces an image which is relatively reduced by a desired factor. If the focal lengths of the collimating and imaging lenses are equal, the length of the refocused image will be relatively reduced by the same factor x although these focal lengths need not of course be equal and could be adjusted to vary magnification in both directions.

It will be appreciated that each beam may be provided with such an arrangement, although certain components of the beam shaping means may be common to a number of beams. Thus in a preferred embodiment a single imaging lens is provided downstream of the beam combining means and which acts therefore on a combined beam, with separate collimating lenses and anamorphic telescopes provided for the laser diode beams upstream of the beam combining means. However it is also envisaged that it may be possible to position a single anamorphic telescope downstream of the beam combining means to act on the combined beam.

There are a number of ways in which the two laser diode beams may be combined. If the wavelengths of the beams differ by any substantial amount, then it may be possible to use a dichroic beam combiner. However since in practice most laser diode sources emit light (e.g. infra red) of around the same wavelength, it is preferred that the beam combination is effected by a polarising beam combiner. A cube constructed from two right angled triangular prisms having their respective hypotenuses in contact and coated in a dielectric material is a particularly simple form of polarising combiner. The beam from one source which is "S" polarised is incident upon the coated surface and reflected therefrom, along the same path as the other beam, which is "P" polarised, is incident on another surface, of the cube and passes straight through the coated surface, to produce a combined beam. Preferably the outer surfaces of the cube have an anti-reflective coating. Other forms of polarising beam combiners are known.

The stripe shaped light beam produced by known laser diodes is polarised in the direction parallel to the stripe axis. Accordingly if the laser diodes are so arranged as to produce images of the stripes which are aligned in the same direction, the polarisation of one beam must be rotated by 90° before it enters the beam combining means. In a preferred arrangement, this may be achieved by inserting a half wave plate in the path of one of the beams. The half wave plate may conveniently be placed in front of a reflecting prism which reflects the respective beam onto the beam combining means. The use of the half wave plate could be avoided by mounting the diodes spatially in a mutually orthogonal arrangement. However, this complicates the mounting of the beam shaping and combining optics in that they have to be mounted orthogonally for the two beams.

As described above, a light source in accordance with the invention is applicable to any number of surgical applications for example contact laser surgery. A source combining laser diode beams into a single fibre is particularly suitable for use in a bundled assembly to provide an enhanced source for a body implantable probe such as an angioplasty device.

Accordingly viewed from a second aspect, the invention provides a light source comprising a plurality solid state laser diodes, optical means associated with a plurality of groups of two or more of said diodes for combining the beams produced by each said group of diodes into a combined beam and focusing each said combined beam into a respective flexible optical fibre, a plurality of such optical fibres being arranged into a closely packed array downstream of the optical means.

This array may be for example a bundle comprising a pair of central fibres surrounded by a number of fibres. The bundle may then be coupled in a suitable manner with a further optical fibre for delivery to a point of use. Where the source is butt coupled to the further fibre, the core diameter and numerical aperture of that fibre should preferably be equal to or larger than that of the array to transmit the light effectively. Similarly if it is to be imaged, the product of the core diameter and numerical aperture of the further fibre should preferably be equal or greater to that of the bundle.

The optical means associated with each laser diode group may include beam shaping, focusing and combining means as described with reference to the first aspect of the invention.

The invention also provides a medical device comprising an optical fibre whose distal end is provided with means for heating body tissue, the proximal end of the fibre being optically coupled to a bundle of fibres forming part of a light source in accordance with the second aspect of the invention. This may be, for example, an angioplasty device having a body implantable fibre.

The combining of laser diodes of similar wavelength into single fibres for power enhancement is itself a new departure from the prior art and viewed from a still further aspect the invention provides a laser diode light source comprising at least two solid state laser diodes, a flexible optical fibre, and optical means, interposed between said diodes and said fibre, comprising means for combining the beams produced by said diodes into a combined beam and means for focusing said combined beams into said fibre, said laser beams being of substantially the same wavelength and being simultaneously focused into said fibre to increase the power output of said source, and said combining means comprising a polarising beam combiner.

A preferred embodiment of the invention will now be described, by way of example only with reference to the accompanying drawings, in which:

FIG. 1 is a plan view of a light source embodying the invention;

FIG. 2 is a side view of the light source shown in FIG. 1, and

FIG. 3 shows, schematically, a plurality of light sources in accordance with the invention formed in a closely packed array.

With reference to FIGS. 1 and 2, two 1 W solid state laser diodes 1, 2 produce light beams 3, 4. Each laser diode in this embodiment has an emitting stripe of $100 \times 1$ $\mu$m in a numerical aperture of $0.1 \times 0.33$. The beams 3, 4 are collimated by collimating lenses 5, 6 and passed through anamorphic telescopes in the form of anamorphic prism pairs 7,8,9,10. As can be seen from the Figures, the anamorphic prism pairs 7,8,9,10 act to initially increase the dimension of the beams 3,4 by a factor of about 3 in the direction parallel to the stripe but do not affect them in the direction perpendicular to the stripe.

After passing through the anamorphic prism pairs 7, 8,9,10 the beams 3,4 are combined in a beam combining cube 11. Cube 11 is constructed from two prisms 12,13 having their respective hypotenuses in contact. The interface 14 is provided with a dielectric coating so that it will transmit light which is 'P' polarised but reflect light that is 'S' polarised.

Since the light beams emitted by the laser diodes 1,2 will both be "P" polarised, at the cube 11, it is necessary to rotate the polarisation of one beam by 90°. To achieve this, the beam 3 is passed through a half wave plate 16 which is arranged on the front face of a prism 17 which reflects the beam 3 onto the interface 14 of the beam combining cube 11.

The dielectric coated surface 14 of the cube 11 is transparent to the beam 4, which accordingly passes through the cube undeflected, but acts as a mirror to the beam 3 which is reflected along the same path as beam 4 to produce a combined beam 18. This beam 18 is then focused by an imaging lens 19 into a flexible optical fibre 20. The imaging lens 19 has the same focal length as the collimating lenses 5,6 and acts, with the anamorphic prisms (7,8,9,10) to produce a combined image of the original light sources 1,2 which is of the same dimension as the originals in the direction perpendicular to the emitting stripe , but which is of a dimension in the direction parallel to the emitting stripe reduced by a factor equal to the increase in thickness of each beam in such direction caused by the prisms. In this particular embodiment, the imaging lens 19 focuses the combined beam to a spot $33 \times 1$ $\mu$m of $0.3 \times 0.33$ NA at the input face of the optical fibre 20 which has a 50 $\mu$m diameter (55 $\mu$m with cladding) of 0.37 NA.

It will thus be seen that the relative length of the image of the emitting stripe of the laser diodes 1,2 has been reduced by a factor of about 3, which means that the shape of the image is a better match with the fibre end and optical fibre 20 may have a correspondingly reduced diameter. Moreover the intensity of the beam incident on the optical fibre 20 is, disregarding losses, substantially double that of the beams produced by individual laser diodes. Also the numerical aperture of the source is closely matched with that of the optical fibre 20.

These factors mean that to produce a source of a given power relatively fewer and smaller fibres will be required, which is of particular importance in angioplasty devices.

FIG. 3 is a top schematic view of a bundled light source which may be used with an angioplasty device.

The source comprises eight light sources 21 (only four shown) each similar to that shown in FIGS. 1 and 2, but with the half-wave plate 16 sandwiched between the beam shaping prism 10 and the reflecting prism 17 and with the prism 8 and the combining cube 11 spaced apart by a glass plate 22 provided therebetween.

The four shown sources 21 are mounted together within the source housing 23 as a module 24. An identical module consisting of the other four sources is invertedly mounted beneath the module 24 shown.

The fibres 20 from the eight sources are bundled together so that two central fibres are surrounded by the other six fibres. This combined source is at 200 $\mu$m diameter and 0.37 NA, and allowing for coupling and transmission losses provides a 10 W source.

The source from this bundle of fibres is then imaged by ball lenses mounted in connector 25 into a single circular fibre 26, the other end of which is coupled to an optical fibre connector 27 mounted on the housing 23, to provide a light source with which a further optical fibre of an angioplasty device may be coupled.

The fibre 25 is of sufficient diameter and numerical aperture for delivery of the light to a point of use such as the distal end of an angioplasty device. The use of such a single circular fibre will also serve to remove at the distal end of the fibre any spatial structure in the light emitted from the array of closely packed fibres caused by variations in the emitted power from the individual fibres within the array and from the discrete structure of the fibre bundle.

Where the source is butt coupled to the further fibre, the core diameter and numerical aperture of the fibre should be equal to or larger than that of the array to transmit the light effectively. Similarly if it is to be imaged, the product of the core diameter and numerical aperture of the further fibre should be equal or greater to that of the bundle.

As an example, the bundle source of this embodiment could be imaged with a magnification of 2 into a fibre of 330 $\mu$m core and 0.19 NA which is suitable for use in angioplasty devices.

It will be understood by the person skilled in the art that the particular numerical values used in the above embodiments are used purely by way of example. It will also be apparent that other amendments may be made which fall within the scope of the invention.

I claim:

1. A laser diode light source comprising:

at least two solid state laser diodes, each of said laser diodes emitting a beam of coherent light in the form of an elongated laser stripe, each said stripe having a length and a width, each said beam having a first numerical aperture in a direction parallel to said stripe length and a second numerical aperture in a direction parallel to said stripe width;

a flexible optical fibre having a input end, said input end having a numerical aperture and a core diameter; and optical means interposed between said laser diodes and said optical fibre for producing a magnified combined image of said laser stripes at said input end of said optical fibre, said combined image having a length and a width, the magnification of each of said laser stripes being less along said length thereof than across said width of said laser stripe, said magnification of each said stripes along said length direction being chosen such that said length of said combined image of said laser stripes does not substantially exceed said core diameter of said optical fibre, said optical means comprising:

beam combining means for combining said beams of coherent light from said laser diodes into a combined beam;

imaging means including focusing means for focusing said combined beam into said optical fibre; and anamorphic beam shaping means for anamorphically shaping said laser beams such that said first and second numerical apertures of said beams are adjusted so that the first and second numerical apertures of said combined beam, in directions parallel to said image length and said image width respectively, do not substantially exceed said numerical aperture of said optical fibre when said combined beam is focused into said input end of said optical fibre.

2. A laser diode light source as claimed in claim 1, wherein the numerical aperture of said combined focused beam substantially matches said numerical aperture of said optical fibre.

3. A laser diode light source as claimed in claim 1, wherein a size of said combined image in said length direction relative to a size of said image in said width direction is reduced by a factor of about three.

4. A laser diode light source as claimed in claim 1, wherein said image stripes are demagnified in said length direction.

5. A laser diode light source as claimed in claim 1, wherein said optical means includes a collimating lens, an anamorphic telescope, and a focusing lens.

6. A laser diode light source as claimed in claim 5, wherein a single focusing lens is provided downstream of said beam combining means to act on said combined beam, and separate collimating lenses and anamorphic telescopes are provided upstream of said beam combining means for each said laser beam.

7. A laser diode light source as claimed in claim 1, wherein said combining means comprises a polarizing beam combiner.

8. A laser diode light source as claimed in claim 7, wherein said laser diodes are oriented such that each said laser beam is polarized in the same direction, and said combining means further comprises a half wave plate through which one of said beams passes prior to the combination of said laser beams in said polarizing beam combiner.

9. A light source combining a plurality of laser diode light sources as claimed in claim 1, said optical fibres being arranged into a closely packed bundle.

10. A light source claimed in claim 1, wherein the numerical aperture of said fibre is approximately 0.37.

11. A medical device comprising:

an optical fibre having a distal end and a proximal end;

means for heating body tissue, said heating means being located at said distal end of said optical fibre; and a light source coupled to said proximal end of said optical fibre, said light source comprising at least one laser diode light source, said laser diode light source including:

at least two solid-state laser diodes, each of said laser diodes emitting a beam of coherent light in the form of an elongated laser stripe, each of said stripes having a length and a width, each said beam having a first numerical aperture in a direction parallel to said stripe length and a second numerical aperture in a direction parallel to said stripe width;

a flexible optical fibre having an input end, said fibre input end having a numerical aperture and a core diameter; and optical means interposed between said laser diodes and said optical fibre input end for producing a magnified combined image of said laser stripes, said combined image having a length and a width, the magnification of each of said laser stripes being less across said length of said laser stripe than across said width of said laser stripe, said magnification of each of said stripes along said length direction being chosen such that said length of said combined image of said laser stripes does not substantially exceed said core diameter of said optical fibre, said optical means comprising:

beam combining means for combining said beams of coherent light emitted by said laser diodes into a combined beam;

imaging means including means for focusing said combined beam into said optical fibre; and anamorphic beam shaping means for anamorphically shaping said laser beams such that said first and second numerical apertures of said beams are adjusted so that first and second numerical apertures of said combined beam, in directions parallel to said image length and said image width respectively, do not substantially exceed said numerical aperture of said optical fibre when said combined beam is focused into said input end of said optical fibre.

12. A laser diode light source comprising:

a) at least two solid-state laser diodes, each said laser diode emitting a laser beam in the form of an elongate laser stripe, each said stripe having a length and a width, and each said beam having a first numerical aperture in a direction parallel to said stripe length and a second numerical aperture in a direction parallel to said stripe width;

b) a flexible optical fibre having an input end, said input end having a numerical aperture and a core diameter;

c) a collimating lens for each said laser diode beam for collimating said laser diode emitted beams;

d) an anamorphic telescope for each said laser diode beam for anamorphically shaping said laser diode emitted beams;

e) polarizing beam combining means located downstream of said collimating lenses and said anamorphic telescopes for combining said laser beams into a single combined beam; and f) focusing means located downstream of said polarizing beam combining means for focusing said combined beam into said fibre;

wherein said collimating means, said anamorphic beam shaping means and said focusing means produce an image stripe of each said laser stripe at said input end of said fibre, each said image stripe having a length and a width, each said image stripe length not substantially exceeding said core diameter of said fibre, and each said image stripe having a length/width ratio less than a length/width ratio of a corresponding laser stripe; and wherein said anamorphic beam shaping means anamorphically shapes said laser beams such that said first and second numerical apertures of said beams are adjusted so that first and second numerical apertures of said combined beam, in directions parallel to said image stripe length and said image stripe width respectively, do not substantially exceed said numerical aperture of said fibre when said combined beam is focused into said input end of said fibre.

13. A laser diode light source comprising:

a) at least two solid-state laser diodes, each said laser diode emitting a laser beam in the form of an elongate laser stripe, each said stripe having a length and a width, and each said beam having a first numerical aperture in a direction parallel to said stripe length and a second numerical aperture in a direction parallel to said stripe width;

b) a flexible optical fibre having an input end, said input end having a numerical aperture and a core diameter;

c) collimating means for collimating said laser diode beam;

d) anamorphic beam shaping means for anamorphically shaping said laser diode beam; and e) means, arranged downstream of said anamorphic beam shaping means, for simultaneously focusing said laser diode beams into said optical fibre;

wherein said collimating means, said anamorphic beam shaping means and said means for focusing said laser diode beams into said optical fibre produce an image stripe of each said laser stripe at said input end of said fibre, each said image stripe having a length not substantially exceeding said core diameter of said fibre, and having a length/width ratio less than a length/width ratio of a corresponding laser stripe; and wherein said anamorphic beam shaping means anamorphically shapes said laser beams such that said first and second numerical apertures of said beams are adjusted so that said beams are able to be efficiently coupled into said input end of said fibre within said numerical aperture of said fibre when said beams are focused into said input end of said fibre.

14. A laser diode light source as claimed in claim 13, wherein said means for simultaneously focusing said laser beams into said optical fibre comprises a focusing lens for focusing said beams into said input end of said fibre.

15. A laser diode light source as claimed in claim 14, further comprising means for combining said beams before they are incident on said focusing lens.

* * * * *